United States Patent [19]
Jarrell et al.

[11] Patent Number: 6,071,610
[45] Date of Patent: Jun. 6, 2000

[54] ENHANCED RESOLUTION MATRIX-LASER DESORPTION AND IONIZATION TOF-MS SAMPLE SURFACE

[75] Inventors: Joseph A. Jarrell, Newton Highlands, Mass.; Michael J. Tomany, Thompson, Conn.; Craig A. Dorschel, Worcester, Mass.

[73] Assignee: Waters Investments Limited

[21] Appl. No.: 08/853,205

[22] Filed: May 9, 1997

Related U.S. Application Data

[63] Continuation-in-part of application No. 08/480,428, Jun. 6, 1995, abandoned, which is a continuation of application No. 08/151,490, Nov. 12, 1993, abandoned.

[51] Int. Cl.[7] ................................................... B32B 5/16
[52] U.S. Cl. ............................................ 428/335; 428/336
[58] Field of Search ............................... 428/332, 336, 428/335; 250/423 P, 288, 281, 282

[56] References Cited

U.S. PATENT DOCUMENTS

| | | |
|---|---|---|
| 4,473,474 | 9/1994 | Ostreicher et al. . |
| 4,527,059 | 7/1985 | Benninghoven et al. . |
| 4,728,796 | 3/1988 | Brown et al. . |
| 4,920,264 | 4/1990 | Becker . |
| 4,988,879 | 1/1991 | Zare et al. . |
| 5,045,694 | 9/1991 | Beavis et al. . |
| 5,118,937 | 6/1992 | Hillenkamp et al. ............... 250/282 |
| 5,135,870 | 8/1992 | Williams et al. . |
| 5,210,412 | 5/1993 | Levis et al. . |
| 5,288,644 | 2/1994 | Beavis et al. . |
| 5,580,434 | 12/1996 | Robotti et al. ......................... 204/451 |
| 5,640,010 | 6/1997 | Twerenbold ........................... 250/281 |
| 5,719,060 | 2/1998 | Hutchens et al. ..................... 436/174 |
| 5,770,272 | 6/1998 | Biemann et al. ...................... 427/421 |

FOREIGN PATENT DOCUMENTS

| | | |
|---|---|---|
| 0 333 912A2 | 9/1989 | European Pat. Off. . |
| 2236185 | 3/1991 | United Kingdom . |
| 2236186 | 3/1991 | United Kingdom . |
| 2257295 | 6/1993 | United Kingdom . |
| PCT/GB90/00973 | 3/1991 | WIPO . |
| PCT/GB90/00974 | 3/1991 | WIPO . |
| PCT/GB90/00975 | 4/1991 | WIPO . |

OTHER PUBLICATIONS

Beavis, R.C. et al., Epitaxial Protein Inclusion in Sinapic Acid Crystals (journal unknown) pp. 442–447 (1993) p. 3, Line 25.

Cornett, D.S., et al., Anal. Chem. 65: 2608–2613 (1993) p. 4, Line 4.

Tanaka, Koichi, et al., Rapid Comm. in Mass Spectr. 2 (8):151–3 (1988) p. 4, Line 1.

T. William Hutchens and Tai–Tung Yip, 41st ASMS Conference on Mass Spectrometry, May 31–Jun. 4, 1993, pp. 781a–781b, New desorption strategies for the mass spectrometric analysis of macromolecules.

Kermit K. Murray and David H. Russell, 41st ASMS Conference on Mass Spectrometry, May 31–Jun. 4, 1993, pp. 780a–780b. Matrix Assisted Laser Desorption Ionization of Aerosols.

(List continued on next page.)

*Primary Examiner*—Hoa T. Le
*Attorney, Agent, or Firm*—Anthony J. Janiuk; Brian Michaelis

[57] ABSTRACT

A thin layer for sample analysis by matrix-assisted laser desorption mass spectrometry, comprising a matrix material in a supported dispersion wherein the support is a solid or is formed from a solid. The invention is also directed to a method of making a thin layer for sample analysis by matrix-assisted laser desorption mass spectrometry, the layer comprising a matrix-solid composition disposed upon a substrate, comprising the step of depositing a solution containing matrix, solid and solvent upon a spinning substrate at a deposition rate sufficient to allow evaporation of the solvent, thereby interspersing the matrix and support on the substrate in a thin layer. Enhanced mass resolution is described.

18 Claims, 9 Drawing Sheets

OTHER PUBLICATIONS

Michael Karas and Franz Hillenkamp, AIP Conference Proceedings, No. 288, Apr. 1993 Knoxville, pp. 447–458, Matrix Laser Desorption Ionization Mass Spectometry—Fundamentals and Applications.

S.J. Doktycz, Rapid Comm. in Mass Spectr. (5), 1991, pp. 145–148, Matrix/Sample Interactions in Ultraviolet Laser–desorption of Proteins.

Graeme J. Currie and John R. Yates III, Journal of Am Society for Mass Spec (4), No. 12, Dec. 1993, pp. 955–963, Analysis of Oligodeoxynucleotides by Negative–Ion Matrix–Assisted Laser Desorption Mass Spectometry.

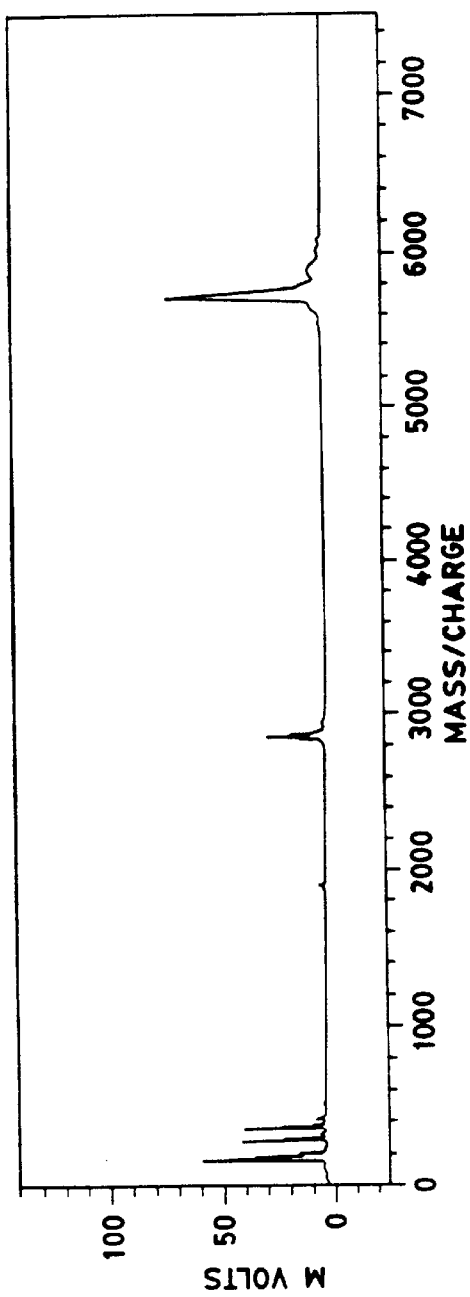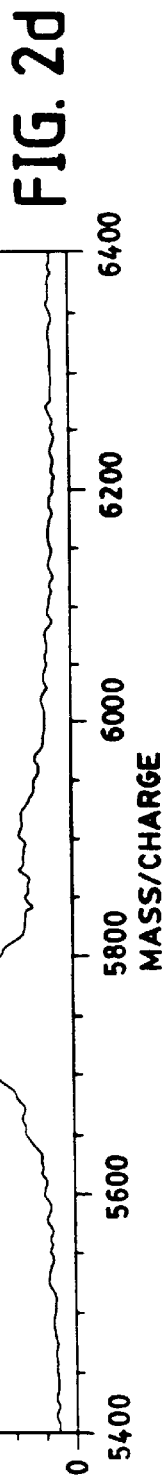

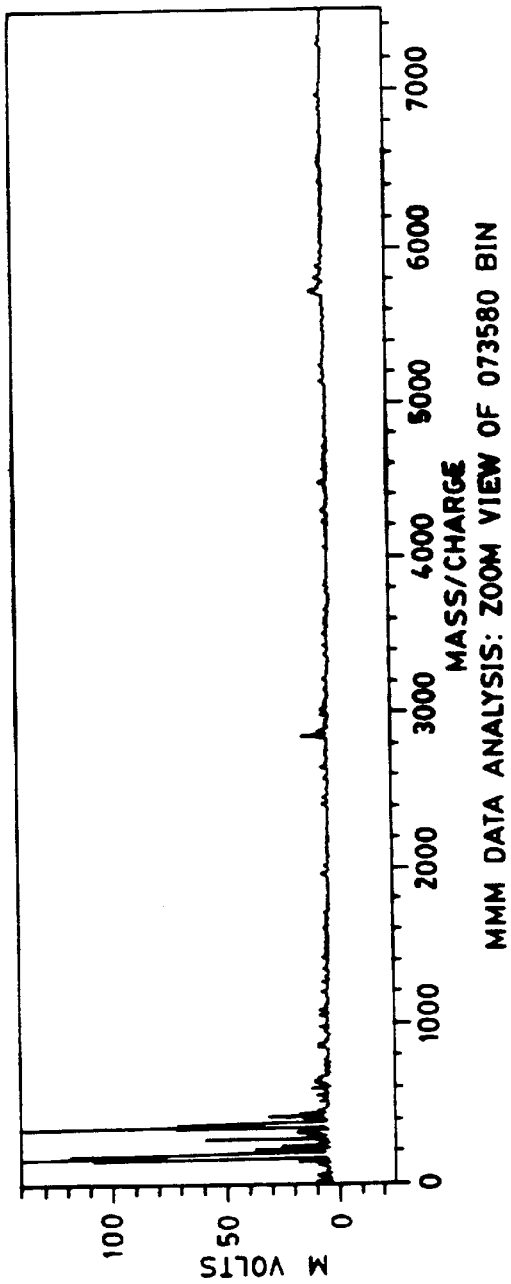
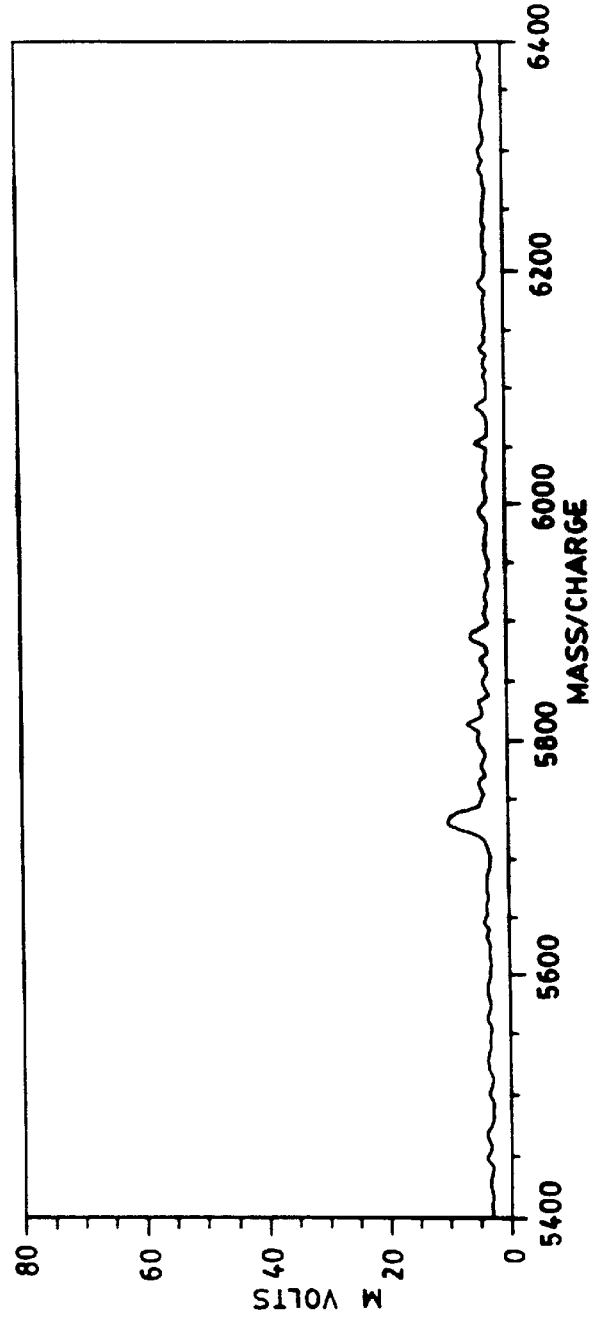

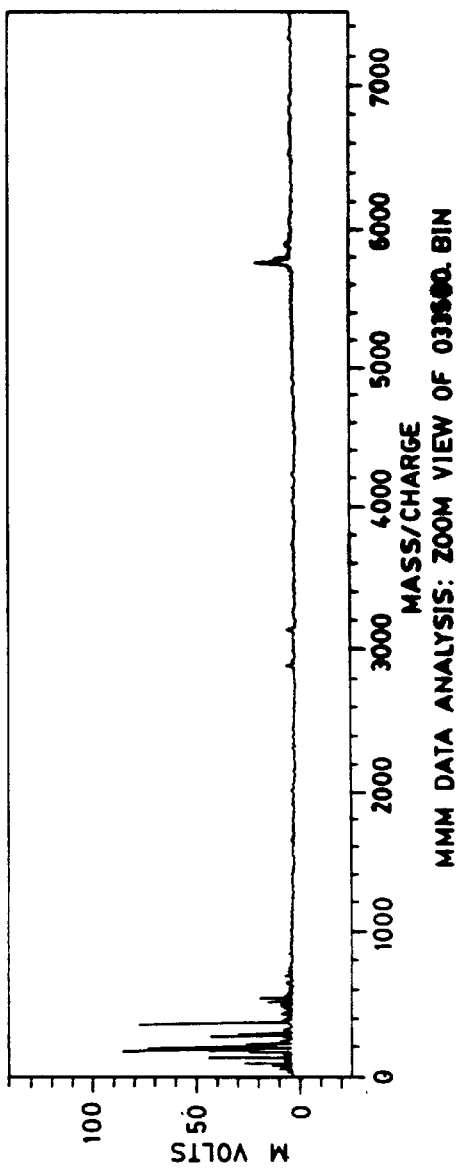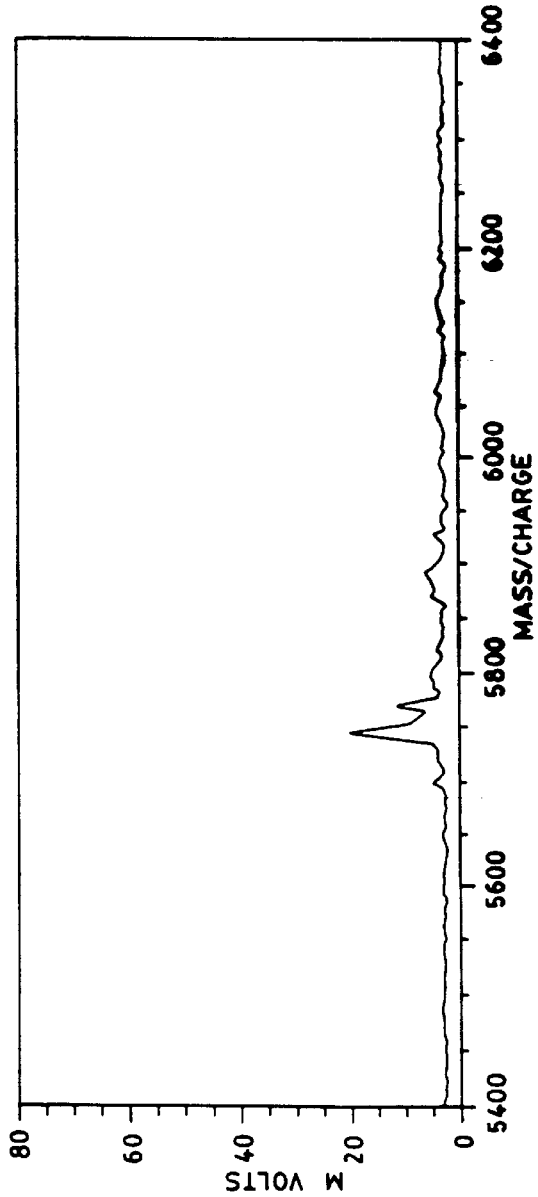

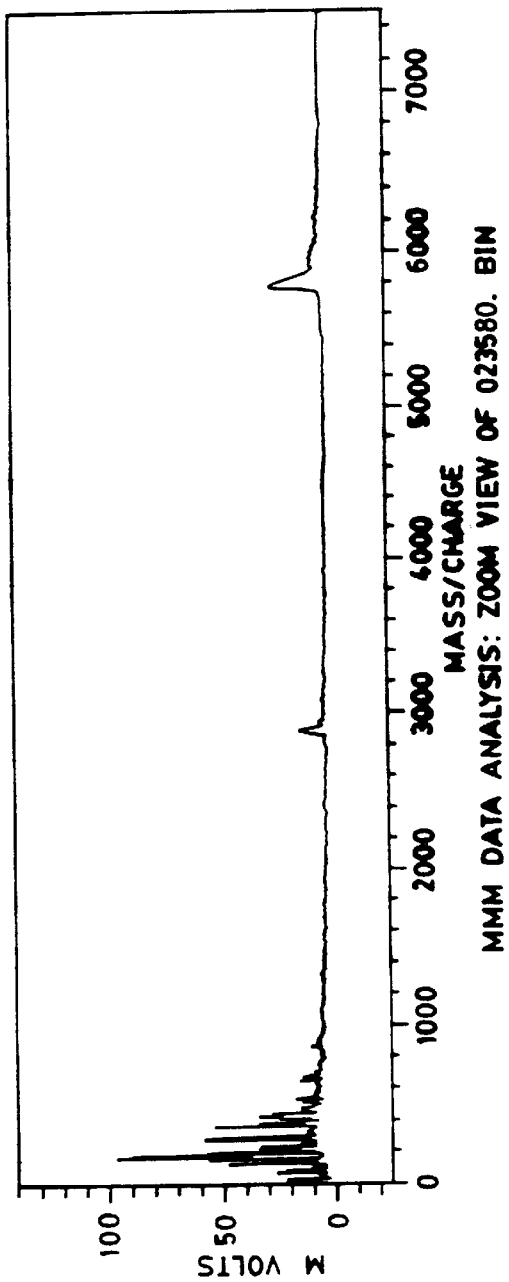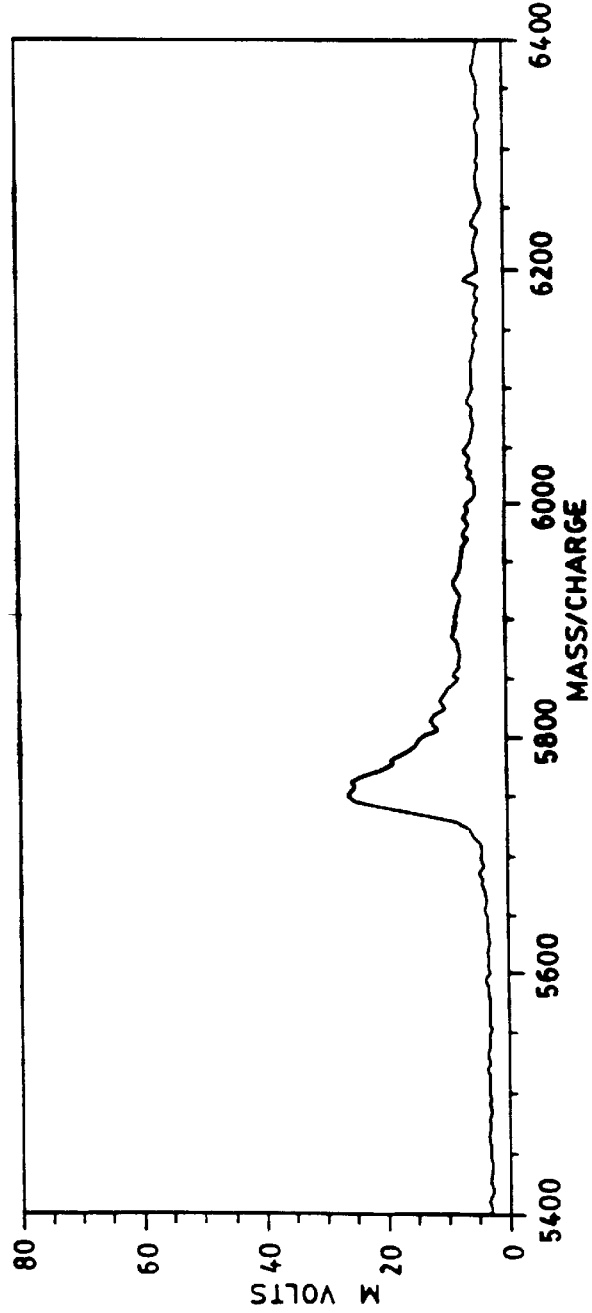

ENHANCED RESOLUTION MATRIX-LASER DESORPTION AND IONIZATION TOF-MS SAMPLE SURFACE

This application is a continuation-in-part of U.S. Ser. No. 08/480,428, filed Jun. 6, 1995, now abandoned which in turn is a continuation of U.S. Ser. No. 08/151,490, filed Nov. 12, 1993, now abandoned.

TECHNICAL FIELD

This invention relates generally to mass spectrometry, and in particular to matrix assisted laser desorption and ionization time-of-flight mass spectrometry. Specifically, this invention relates to a method and apparatus for improved sample desorption by laser excitation that results in greatly enhanced mass resolution and sensitivity for a time-of-flight system.

BACKGROUND ART

Matrix-assisted laser ionization and desorption time-of-flight mass spectrometry is a recently developed technique which is particularly useful for the sensitive analysis of large biomolecules. The matrix is a material that assists in the transfer of energy to the analyte molecule, allowing it to be ionized without significant fragmentation, and leave the surface of a target that is being irradiated with a laser. Typically, a few microliters of a solution containing sample molecules at concentrations of about 1 $\mu g/\mu L$ are mixed with 10–20 $\mu L$ of a solution containing matrix molecules at concentrations of about 10 $\mu g/\mu L$. A few microliters of this mixture are then deposited on a suitable substrate and dried in air.

As the sample dries, crystals of matrix are formed and the sample is thought to be incorporated into the crystal. The substrate is then introduced through a vacuum lock into a time-of-flight mass spectrometer system. In such systems, a high voltage source (often 30 KV or more) will be connected to the substrate.

Once the sample has been introduced into the mass spectrometer, a pulsed laser is used to irradiate the sample on the substrate. The interaction of the laser radiation with the matrix molecules leads, by a process that is only partly understood today, to the formation and desorption of largely intact, ionized sample molecules. Predominantly these ions are of a type known as (M+H)+ ions, that is, the neutral sample molecule (M) is ionized by the attachment of a proton. This ionization process has some similarity to the process called "chemical ionization" used conventionally in gas chromatography/mass spectrometry.

Most frequently these ions are analyzed in so-called linear time-of-flight (TOF) mass spectrometers. The ions, once formed, are accelerated by an electric field and then allowed to travel in straight lines until they are detected. The transit time between ion formation and detection can be used to determine the mass of the species from which the ions are generated. Typical linear TOF systems are described in U.S. Pat. No. 5,045,694 (Beavis and Chait). Such linear devices provide only modest mass resolving power, e.g. 50–800, because they are unable to compensate for various known aberrations. A dominant aberration in such linear systems stems from the fact that the ions are formed with a wide distribution of initial velocities. This means that for an ion of a given mass there will be a distribution of arrival times at the detector that will limit the mass resolving power of such a device, since ions with more initial velocity in the forward direction will arrive sooner than ions with less initial velocity.

Techniques for compensating for such aberrations resulting from the initial velocity distribution in TOF mass spectrometers are well-known. The primary technique is to provide an electrostatic mirror, called a reflectron, which reverses the direction of travel of the ions in such a way that the effects of these initial velocity distributions on ion transit times are eliminated. A recent review article describing such devices is "Time-of-flight Mass Spectrometry: An increasing Role in the Life Sciences", R. J. Cotter, Biomed. Env. Mass Spectrom., 18: 513–532 (1989). The practice of matrix-assisted laser desorption and ionization in reflectron-based instruments is also known and typically produces mass resolutions of 2000–4000 for molecules less than 5000 Daltons in molecular weight.

In both linear and reflectron-based TOF instruments, it is thought that a significant factor limiting mass resolution is the interaction of sample ions with other desorbed matrix ions and molecules i.e., as the desorbed biomolecules leave the surface of the target, they may encounter a plume of matrix ions and molecules. Interactions with this plume may change the energy of desorbed biomolecule ions, but not in a homogeneous manner. Some biomolecules may gain more kinetic energy, some may lose kinetic energy. Thus, the time of arrival of the biomolecules is not exactly the same because some are flying faster, and some slower, than the mean. The net result is band broadening and a concomitant loss in mass resolution. To date, the inventors are not aware of efforts to narrow the initial velocity distribution by manipulation of the matrix. Crystal formation occurs as the sample/matrix mixture dries down in a largely uncontrolled manner. It is postulated that this leads to variability in the analysis of the sample. In addition, the necessity of mixing sample with matrix prior to dry down often results in inefficient use of sample. Accordingly, it would be desirable to provide methods and apparatus for providing greater consistency in the sample preparation process and more efficient use of sample.

Hillenkamp et al., in British Patent Nos. GB 2236185A, and GB 2236186A, disclose surfaces and matrices for laser desorption of biomolecules from surfaces. GB 2236185A discloses a two-dimensional layer comprising a matrix ("absorbing component") underlying the substrate. The application is aimed at macromolecular blotting. GB 2236186A discloses desorption of biomolecules using 337 nm or higher laser radiation on a similar surface. Sinapinic acid is shown as the matrix.

Cottrell, PCT/GB90/00973, discloses a method for preparing a sample for analysis by LDMS that includes electrospraying the matrix (nicotinic acid) onto a target surface, then sample in TFA is applied and dried down. Finally, the sample is introduced into the mass spectrometer and a laser is directed onto the sample, desorbing the sample.

Cottrell, PCT/GB90/00974, discloses a method for preparing a sample for analysis by LDMS that includes electrospraying a substrate (nitrocellulose) onto a target, depositing a sample dissolved in aqueous 0.1% trifluoroacetic acid (TFA), and then drying it down. Matrix material (nicotinic acid, 30 mM in acetone) is then applied in droplet form to cover the dried-down sample and dissolve the substrate nitrocellulose. Sample, substrate and matrix dry down together in an intermixed form. If the sample is a protein, the protein adsorbs to the nitrocellulose by hydrophobic interactions. Loss of mass resolution is caused when excess matrix is evaporated from the surface of the target, causing the plasma effect described supra.

Cottrell, PCT/GB90/00975, additionally discloses the use of various matrix materials such as cinnamic acid, benzoic acid, or coumarin in the methods disclosed above.

Beavis, J. Phys. D: Appl. Phys., 26(3), 442–7, has emphasized the desirability of crystal formation.

Hutchens (Proceedings of the 41st American Society of Mass Spectrometry Conference on Mass Spectrometry and Allied Topics, May 31–Jun. 4, 1993, pp. 781a–781b) has described a technique called Surface-Enhanced Neat Desorption (SEND), in which energy-absorbing molecules are covalently bonded to an inert substrate, allegedly providing a matrix-free method for introducing large molecular weight biopolymers into the gas phase without fragmentation. However, this technique appears to have limited reproducibility.

Other efforts to laser desorb biomolecules include those of Tanaka et al. (Rapid Commun. Mass Spectrom. 2, 151–153, (1988)) who describe a system for matrix-assisted laser desorption and ionization in which the sample is dissolved in glycerol containing small cobalt particles. Cornett et al, Anal. Chem. 65: 2608–2613 (1993) has described a system in which various energy absorbing molecules such as rhodamine 6G are dissolved along with the sample molecules in a liquid matrix such as 3-nitrobenzyl alcohol.

Williams in U.S. Pat. No. 5,135,870 and Becker in U.S. Pat. No. 4,920,264 describe systems involving frozen layers of ice for the desorption and ionization of DNA. None of these systems have demonstrated surprising resolution to date.

Thus the need exists for a laser desorpt on matrix composition that can decrease the loss in mass resolution that occurs when using prior art procedures as well as provide increased sensitivity.

SUMMARY OF INVENTION

The present invention overcomes the disadvantages and limitations of the prior art by providing a surprising enhancement in mass resolution comprising a thin-layer for sample analysis by laser desorption mass spectrometry wherein the band-broadening contribution due to the matrix substrate sample composition is minimized. In accordance with the invention, mass resolution and sensitivity are increased by the use of a thin layer comprising a matrix material in a supported dispersion wherein the support is a solid or is formed from a solid. The solid support is preferably a solid that limits matrix crystal growth, most preferably a polymer. Thicknesses not greater than 1 $\mu$m are most preferred.

The preferred embodiment of the invention is a thin layer for sample analysis by matrix assisted laser desorption mass spectrometry, comprising a matrix-polymer composition disposed upon a substrate. Any matrix material may be used, but Sinapinic acid or α-cyano-4 hydroxycinnamic acid is preferred. The matrix-polymer composition may include a polymer selected from the group consisting of cellulose acetate, cellulose nitrate, and polycarbonate. However, other polymers are also possible. The matrix-polymer composition may preferably range from about 70% polymer to about 30% polymer. Preferably, it is 50%. The mass resolution of the sample is significantly enhanced using this invention, and unexpected mass resolutions of over 8000 have been demonstrated in a linear 150-cm flight tube machine.

The invention is also directed to a device for performing matrix-assisted laser desorption mass spectrometry of sample molecules, comprising a substrate capable of receiving on its surface a thin layer as previously described. The device is combined with a solution of sample molecules wherein the sample and matrix are substantially coplanar, and then subjected to mass analysis.

The substrate underlying the device is selected from the group consisting of glass, ceramic, plastic, metal, or similar materials. The thin layer of the device is resistant to decreased mass resolution and sensitivity over time, i.e., it has a substantial shelf life.

The invention is also directed to a method for making a thin layer for sample analysis by matrix-assisted laser desorption mass spectrometry, the thin layer comprising a matrix material in a supported dispersion wherein the support is a solid, comprising the steps of: depositing a solution containing matrix, support and solvent upon a substrate; and then evaporating the solvent, thereby interspersing the matrix and support on the substrate in a thin layer. The preferred method is spin casting, however other methods are also possible. The product made by this process is also a part of this invention.

BRIEF DESCRIPTION OF DRAWINGS

FIGS. 2a–2d are mass spectra obtained from an insulin sample deposited on a thin film of cellulose acetate and matrix on a glass disc substrate;

FIGS. 3a–3d are mass spectra obtained from an insulin sample prepared by conventional means, deposited and dried on a glass disc;

FIGS. 4a–4d are mass spectra obtained from an insulin sample deposited on a thin film on a glass disc substrate (an alternative embodiment);

DETAILED DESCRIPTION OF THE INVENTION

Figure 1:
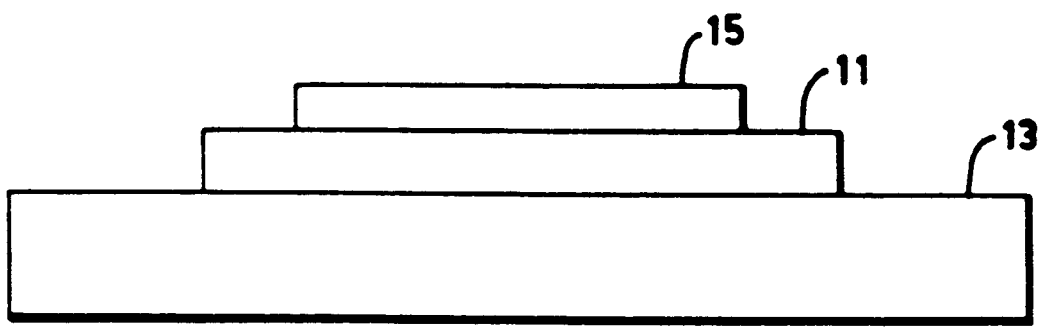
FIG. 1 depicts a sample, thin film and substrate embodying features of the present invention.

The invention will be described in part by referring to the attached figures. The invention is directed to a thin layer for sample analysis by matrix-assisted laser desorption mass spectrometry, comprising a matrix material in a supported dispersion wherein the support is a solid or is formed from a solid. FIG. 1 illustrates the features of the present invention. As depicted, in cross-section, a film 11 is formed or deposited on a substrate 13. A sample 15 is placed on the film. The film comprises crystals of a matrix material dispersed in a support material. The substrate 13, sample 15 and film 13 are placed in a laser desorption mass spectrometer for analysis. The term "supported dispersion" refers to a solid support for maintaining the matrix in a dispersed state in which large crystal formation is inhibited. A preferred embodiment is a thin film of matrix comprising α-cyano-4-hydroxycinnamic acid and polymer comprising cellulose acetate, having a thickness of not greater than 1 $\mu$m. Other matrices and solids, including polymers, may be used. For matrices, these may include, but are not limited to, thymine, pyrazinecarboxylic acid, thiourea, nicotinic acid, vanillic acid, ferulic acid, caffeic acid, sinapinic sacid, dihydrobenzoic acid, and other derivatives of these acids. See GB 2236185A (Hillenkamp et al.) for other matrices.

Polymers that may come within the scope of this invention broadly include all those that may be used in the process of making the matrix-polymer thin film, as described below. These polymers may include cellulose acetate, cellulose nitrate, polycarbonate, nylon, PVDF and any that may conveniently be prepared as solutions. The specific combination of matrix and polymer does not appear to be critical. Sinapinic acid and α-cyano-4-hydroxycinnamic acid are preferred matrices, while polycarbonate, cellulose acetate, and cellulose nitrate are preferred polymers. One function of the polymer appears to be to inhibit formation of large, thick crystals of matrix.

The solvent used to deposit both matrix and solid must be able to solubilize both. For cellulose acetate and α-cyano-4-hydroxycinnamic acid, acetone is preferred. For cellulose nitrate, 75% ether/25% ethanol is preferred. For polycarbonate, tetrahydrofuran is preferred. One of ordinary skill will be able to determine a suitable solvent for solubilizing both matrix and polymer.

The choice of material for a substrate onto which these films of matrix and polymer are deposited is not critical and various materials may have different advantages in different analytical situations. Stainless steel, glass and quartz discs are preferred embodiments. Ceramic, plastic and other compositions, porous and non-porous surfaces, are likely to work. Further, it may be useful to impregnate matrix into a thin surface layer, either as a dissolved species or into small voids, into or onto a thick material such as a polymer sheet that can readily be punched into conveniently shaped substrates.

It is possible that having a substrate that would control the thickness of the matrix-sample mixtures in these systems would be beneficial. This could be a porous polymer substrate, or any substrate that would absorb and retain the matrix-sample mixture in a thin layer. Microreticulated surfaces are specifically contemplated.

The thickness of these films is believed to be an important aspect of the invention. Increased mass resolution is shown in those films which comprise a thin layer, i.e. having thicknesses under 2 $\mu$m. The range of thicknesses over which this invention is operable is from 5 to 0.005 $\mu$m. A preferred range is from 2 to 0.1 $\mu$m, and the most preferred range is from 1 to 0.05 $\mu$m. Scanning-electron micrographs of films of the matrix α-cyano-4-hydroxycinnamic acid and cellulose acetate were obtained by taking glass discs onto which had been deposited thin films, and fracturing them so that the films could be observed in cross-section and thickness measured. Films having a cross-sectional thickness of approximately 0.09 $\mu$m, 0.37 $\mu$m and 2.2 $\mu$m were made. The film having a thickness of 0.09 $\mu$m was prepared in a similar fashion except that the substrate was spun at roughly 30,000 rpm instead of 5000 rpm resulting in a thinner film. Spectra obtained from sample deposited on such a film can provide high resolution, but signal is sometimes not as uniform across the substrate. A thick film, approximately 2.2 $\mu$m thick, provides lower resolution and lower sensitivity spectra.

The exact reason for this increased performance is not completely evident at this point, but it is likely that several different factors are relevant. Although the invention is not limited to any particular theory, the following may explain the observed results. One model for the matrix assisted desorption and ionization process proposes that it is necessary for the solid matrix to be converted to a gaseous plume by absorbing incident laser radiation which then serves to expel the sample molecule or ion into the vacuum (A. Vertes et al, "Expansion Cooling in Matrix Assisted Laser Desorption—a Hydrodynamic Study," Proceedings of the 39th American Society of Mass Spectrometry Conference on Mass Spectrometry and Allied Topics May 19–24, 1991, pp. 927–928). For the molecules that are absorbing energy from the heated matrix, it is usually true that the thickness of matrix crystals will affect how quickly their temperature will rise, i.e., thicker objects take longer to get hot. Accordingly, having a thin film may help ensure that all ions are created at closer to the same time. Thus, it is possible that having the sample and matrix contained in a uniform thin film, as opposed to the relatively thick, jagged, three dimensional crystals of the prior art, may improve the likelihood that all ions formed start closer to the same place and at the same equipotential in the acceleration region. This obviously would help improve resolution.

Alternatively the same model proposes that as sample ions are formed and accelerated in the acceleration region of the mass spectrometer, they undergo collisions with neutral and charged matrix molecules and ions and that these collisions contribute to an energy "spread" of the ion population. It is therefore possible that ions formed from sample molecules in or contiguous to a thin film of matrix will undergo fewer collisions and thus suffer less energy spread. It may well be that the importance of the relatively inert polymer in this film is to provide mechanical integrity, but also to prevent the aggregation of the matrix into large structures when the sample molecule solvent is applied and thus to maintain the sample molecules and the matrix molecules in a physically constrained and hence thin environment. This explanation is consistent with the improved resolution demonstrated in FIGS. 2a through 2d relative to FIGS. 3a through 3d discussed supra.

The invention also includes a method of making a thin layer for sample analysis by matrix assisted laser desorption mass spectrometry, the layer comprising a matrix material in a supported dispersion wherein the support is a solid, comprising the steps of depositing a solution containing matrix, solid and solvent upon a substrate, and then evaporating the solvent, thereby interspersing the matrix and support on the substrate in a thin layer. The method is accomplished by depositing roughly 10 $\mu$L of a solution of 30 mg/ml of a polymer, most preferably cellulose acetate, and 30 mg/ml of a matrix, most preferably α-cyano-4-hydroxycinnamic acid, onto a substrate, preferably a glass or metal disc roughly 0.5" in diameter, spinning at roughly 5000 rpm. The resulting film dries rapidly (typically less than a few seconds) and is usually less than 1 $\mu$m thick. These discs may be stored and used at a later time. Thickness of the film is controlled by the concentration of the α-cyano-4-hydroxycinnamic acid and cellulose acetate in solution; the rate of spinning; and the rate of solvent evaporation. Spin casting is only one method of making the thin film; others such as electrospray deposition (See WO 91/02961) and chemical vapor deposition are within the knowledge of one of ordinary skill in the art.

A sample molecule such as bovine insulin was applied by dispensing a small volume, 0.5 $\mu$L is typical, of an insulin solution onto the substrate and then allowing it to dry in air such a film, after a sample of 0.5 $\mu$L of a solution of 0.001 $\mu$g/$\mu$L of insulin in water and 0.1% trifluoroacetic acid has been deposited on it and allowed to dry, is then be introduced into a laser desorption time-of-flight mass spectrometer.

Figure 2A:
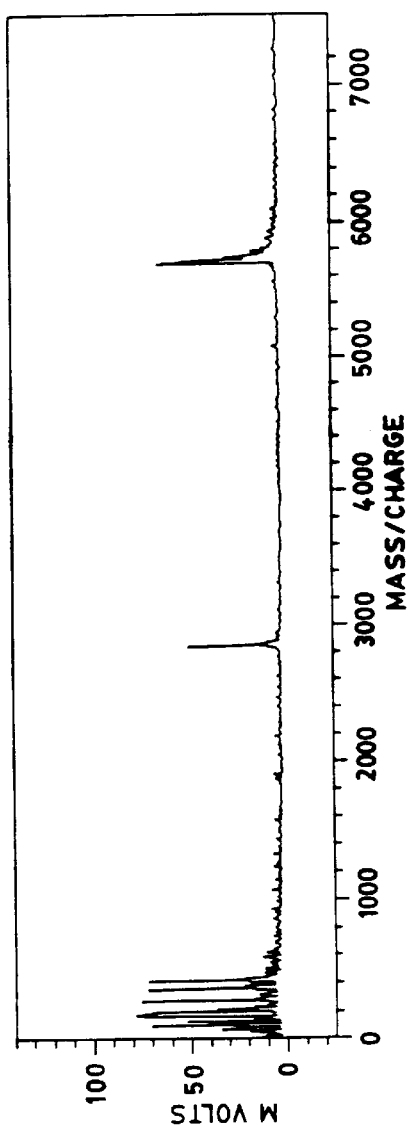
Figure 2B:
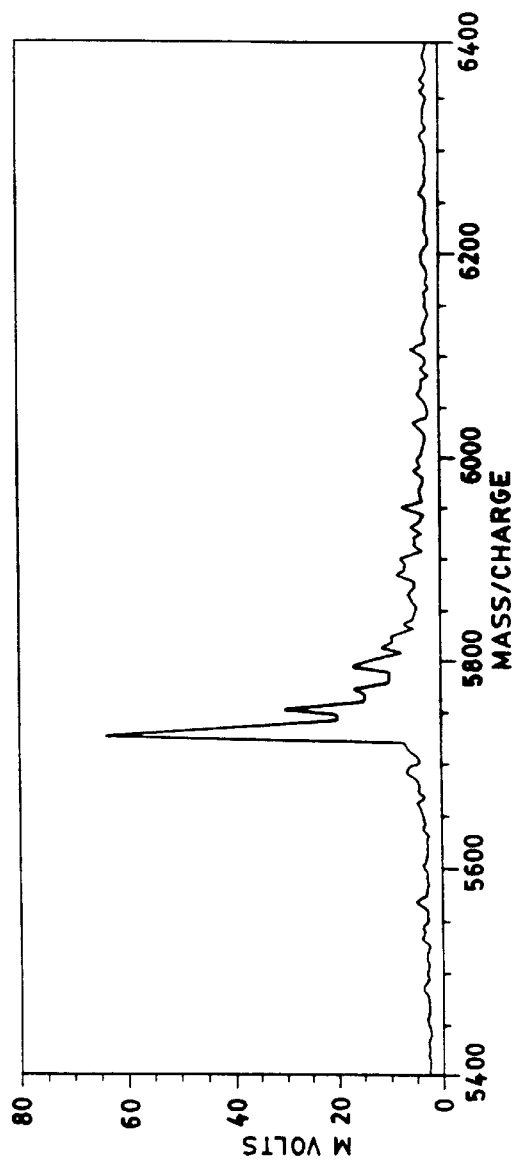

Mass spectra obtained from such a sample are shown in Example 1 (FIGS. 2a through 2d). The spectra shown in FIG. 2a was acquired with two laser shots from a nitrogen laser emitting at 337 nm (see Materials under Examples). FIG. 2b depicts magnified or zoom view of the peak A of FIG. 2a at approximately 5700 mass charge. Other lasers emitting at different frequencies are also possible, and well known to those of ordinary skill. The spectrum shown in FIG. 2c was acquired by scanning the laser beam across the sample and averaging together only those spectra which had an insulin peak above a certain threshold intensity. The spectra at 2d depicts a magnefied or 200 m view of the peak of FIG. 2c at approximately 5700 mass/charge.

Figure 3C:
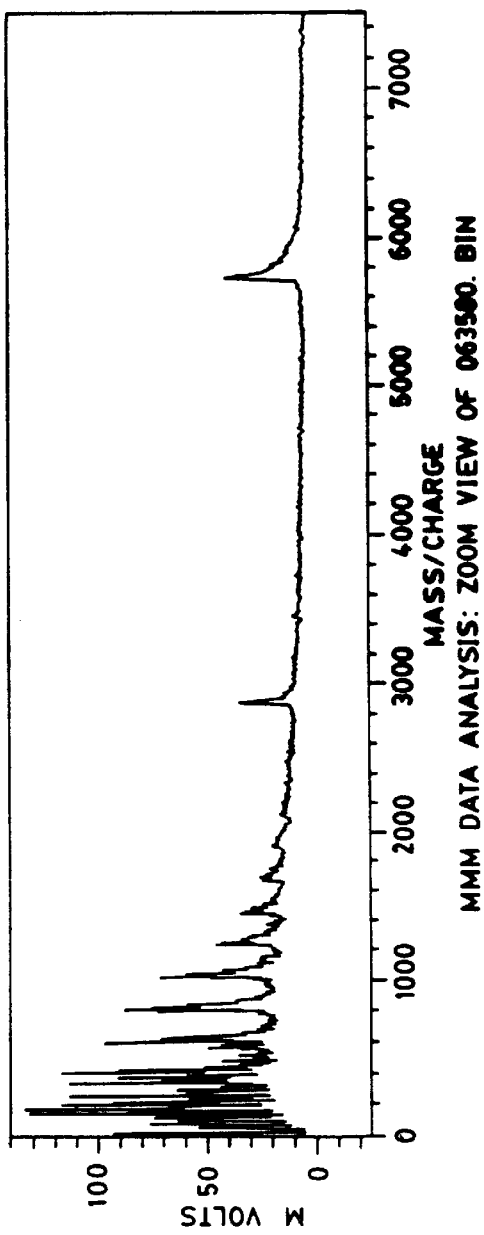
Figure 3D:
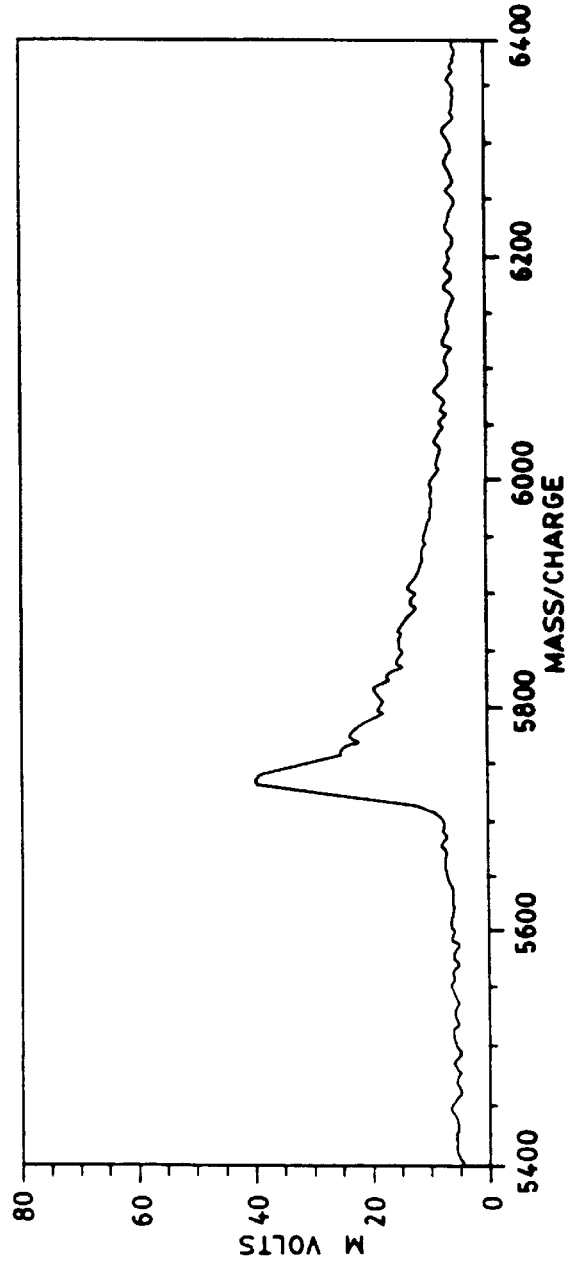

Spectra obtained from such samples show much better mass resolution and reproducibility than spectra obtained from samples prepared by the most common prior art technique, which does not show a thin layer of polymer-matrix. Mass resolution is defined as the mass (parent ion mass) divided by the mass represented by the width of the peak at half of its height. This may be seen by comparing FIGS. 2a through 2d to FIGS. 3a through 3d respectively. FIGS. 3a and 3c depict spectra acquired using a prior art matrix material. FIGS. 3b and 3d are magnified or zoom views of the peaks of FIGS. 3a and 3c at approximately 5700 mass/charge. The former and the latter spectra were obtained in the same instrument and with the same initial instrument parameters. It should be noted that 10 times as much insulin was deposited on the disc used to obtain the prior art FIGS. 3a and 3d as was deposited on the disc used to obtain FIGS. 1a, and 1d, highlighting the fact that surprizingly increased sensitivity is also a hallmark of this invention.

Figure 5:
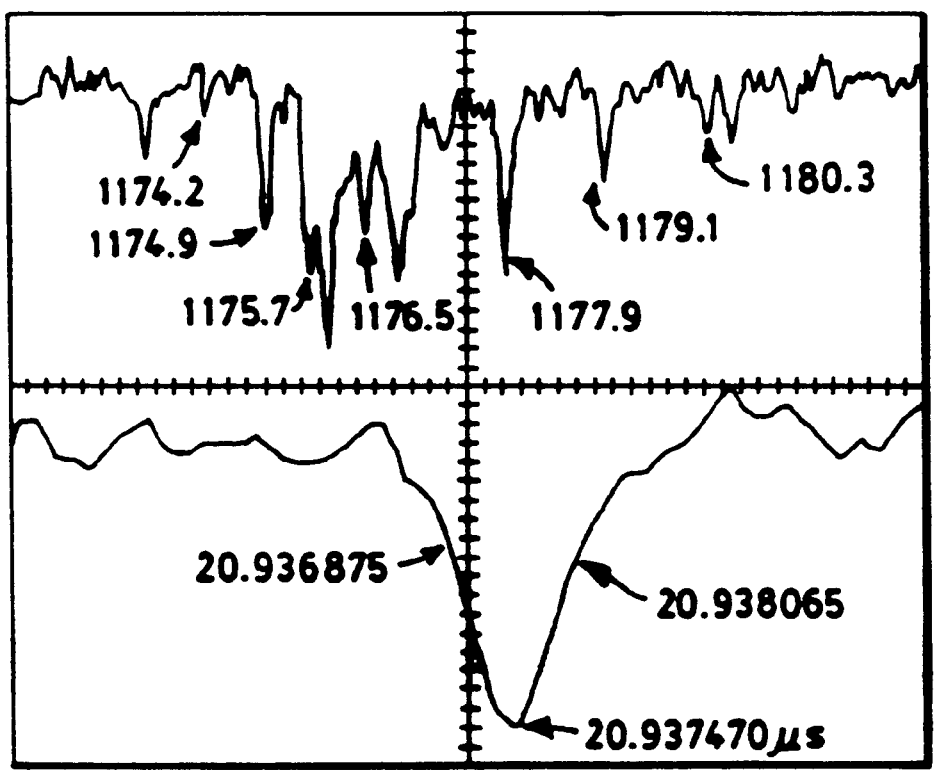
FIG. 5 is a high-resolution mass spectrum of a sample of maltoheptaose deposited on a preprepared substrate similar to that one used to generate FIGS. 2a through 2d.

A further embodiment is shown by FIGS. 4a, through 4d. These figures were obtained in a manner similar to FIGS. 2a, through 2d, except that no cellulose acetate was used. Thus a thin film consisting only of α-cyano-4-hydroxycinnamic acid was deposited on the quartz substrate. Thus, FIGS. 4a and 4c depicts a spectra using a thin film without cellulose acetate. FIGS. 4b and 4d depict magnified or zoom views of the peaks of FIGS. 4a and 4c at approximately 5700 mass/charge. While the mass spectral results obtained were better than those obtained by conventional means displayed in FIGS. 3a through 3d, these results are not as good as those displayed in FIGS. 2a and 2b. Further evidence of the increased mass resolution conferred by this invention is shown in FIG. 5. A similar linear time-of-flight mass spectrometer was used on a sample of the oligosaccharide maltoheptaose, except that in this case the flight tube length was approximately 1.5 m and the ion detector used was a dual chevron channel plate assembly such as the #F TO-2003 time-of-flight detector sold by Galileo Electrooptics. The essential characteristic of this detector is that it has a very fast response time and a 50Ω output impedance. In addition a higher speed digitizer, such as LeCroy #9360 sampling at 5 GHz with an analog bandwidth of 300 MHz was used.

Sugars typically have a greater proclivity for sodium ions, as opposed to peptides which have a greater tendency to ionize by the addition of a proton. Consequently the peaks shown in FIG. 4 are what are known as (M+Na)+ ions. This spectrum was the average of those produced by five laser shots. There is some uncertainty with regard to the full interpretation of this spectrum, i.e., there are some extra peaks that are not readily assigned to a known species. What is clear, however, is that this spectrum clearly demonstrates the ability of samples prepared by this invention to be analyzed with higher mass resolution than has hitherto been demonstrated in a linear time-of-flight machine of this length. The individual maltoheptaose species that result from the distribution of the natural abundance of $^{13}C$ are resolved. In addition, by inspecting the peak labeled with the mass 1177.9 and expanding it as is the lower trace, it is evident that the mass 8797 is calculated by measuring the full width at half height of the peak relative to the arrival time of the peak. This is roughly an order of magnitude greater than has hitherto been observed in any linear machine of comparable length for ions created by matrix-assisted laser desorption and ionization and even exceeds that obtainable in most reflectron-based instruments.

Other adaptations of this technology to the mass analysis of macromolecules may develop according to these scenarios. Seliergren et al., J. Chromatogr. 347:1–10, (1985); Glad etal., J. Chromatogr. 347:11–23, (1985) and Dabulis et al, Biotechnology and Bioengineering, 39(2): 176–185 (1992) have each proposed different ways of "molecular imprinting." Molecular imprinting is a method of synthetically generating binding sites with some degree of specificity for 12 other molecules by creating a mold or pocket in another material such as a plastic, so that sample molecules may be held and hence concentrated. Hutchens et al, Rapid Commun. Mass Spectrom. 7: 576–580, (1993) have demonstrated the use of single stranded DNA as an affinity capture surface to concentrate species of interest for laser desorption. DNA and other large biological molecules such as antibodies, however, are often complex and fragile. The methodologies of molecular imprinting, however, can produce inexpensive rugged binding sites made from inert robust materials and such imprints may have value, particularly in diagnostic applications. Thus it may be advantageous to use such binding materials in conjunction with matrix assisted laser desorption and ionization. Specifically, small plastic particles can be prepared by well known techniques that contain molecular imprints of molecules of interest. It may thus be useful to incorporate such beads into thin films of matrix and possibly other inert materials in ways that do not destroy the molecular imprint such as by dissolving the matrix and any other materials in a solvent that does not dissolve the beads.

Thus it is likely that other means of generating a thin sample-matrix combination may be effective. For example, a micro-reticulated surface such as can routinely be generated on glass or silicon (or by molding plastics or epoxies from masters) when coated with a thin film of matrix, may prove to be an effective substrate, the micro-reticulation serving to prevent the aggregation of matrix and/or sample when the sample is deposited. Likewise laminated structures consisting of thin, and if necessary porous, layers of matrix and an inert substance may be effective. Alternatively, it may be possible to form pre-prepared substrates by coating or polymerizing the inert material around small preformed matrix crystals or particles. It may also be appropriate and convenient to polymerize matrix monomers (or more generally energy absorbing monomers) around predeposited sample molecules. It will also be evident that these thin films need not be continuous, e.g. thin patches of such films may work too.

Having now generally described this invention, the same will become better understood by reference to certain specific examples which are included herein for purposes of illustration only and are not intended to be limiting unless otherwise specified. All U.S. patents cited herein are fully incorporated by reference in their entirety.

EXAMPLES

Materials

All spectra displayed in FIGS. 2a–2d, 3a–3d and 4a–4d were obtained by introducing the respective samples into a linear time-of-flight mass spectrometer with a flight tube length of approximately 55 cm and a fast response time response discrete dynode electron multiplier, such as Model # AF820H manufactured by ETP PTY Ltd., with the last few dynodes buffered by extra capacitance. Pulses of laser radiation at 337 nm from a nitrogen laser such as is Model

VSL337ND manufactured by L.S.I. were used for the matrix-assisted desorption and ionization. The output of the electron multiplier was sampled at 100 M samples/sec by a nominal 8 bit digitizer with an analog bandwidth of 300 MHz such as is offered by several manufacturers such as LeCroy Inc. Bovine insulin was obtained from Sigma (St. Louis, Mo.). Sinapinic acid and α-cyano-4 hydroxycinnamic acid were obtained from Aldrich Chemical Co. (Milwaukee, Wis.).

Example 1

Construction of a Thin Films of α-cyano-4-hydroxycinnamic acid and Cellulose Acetate This example is a preferred embodiment and is discussed in reference to FIGS. 2a–2d, and 5. A thin film of α-cyano-4-hydroxycinnamic acid and cellulose acetate was prepared by dropping roughly 10 uL of a solution of 30 mg/ml of cellulose acetate and 30 mg/ml of α-cyano-4hydroxycinnamic acid onto a glass disc spinning at roughly 5000 rpm. The glass disc was spun by mounting it onto a Dremel (Racine, Wis.) Moto-tool Model 395 type 3. The resulting film dried rapidly (typically less than a few seconds) and is typically less than 1 μm thick. These discs may be stored and used at a later time. Typically a sample such as insulin may be applied by dispensing a small volume, 0.5 μL is typical, of an insulin solution onto the substrate and then allowing it to dry in air. After a sample of 0.5 μL of a solution of 0.001 μg/μL of insulin in water and 0.1% trifluoroacetic acid has been deposited on it and allowed to dry. This dried sample was then introduced into a laser desorption time-of-flight mass spectrometer. Mass spectra obtained from such a sample are shown in FIGS. 2a through 2d. The spectrum shown in FIGS. 2a and 2b was acquired with two laser shots. The spectrum shown in FIGS. 2c and 2d was acquired by scanning the laser beam across the sample and averaging together only those spectra which had an insulin peak above a certain threshold intensity. Spectra obtained from such samples show surprisingly better mass resolution and better reproducibility than spectra obtained from samples prepared by the most common prior art technique.

Example 2

Figure 6A:
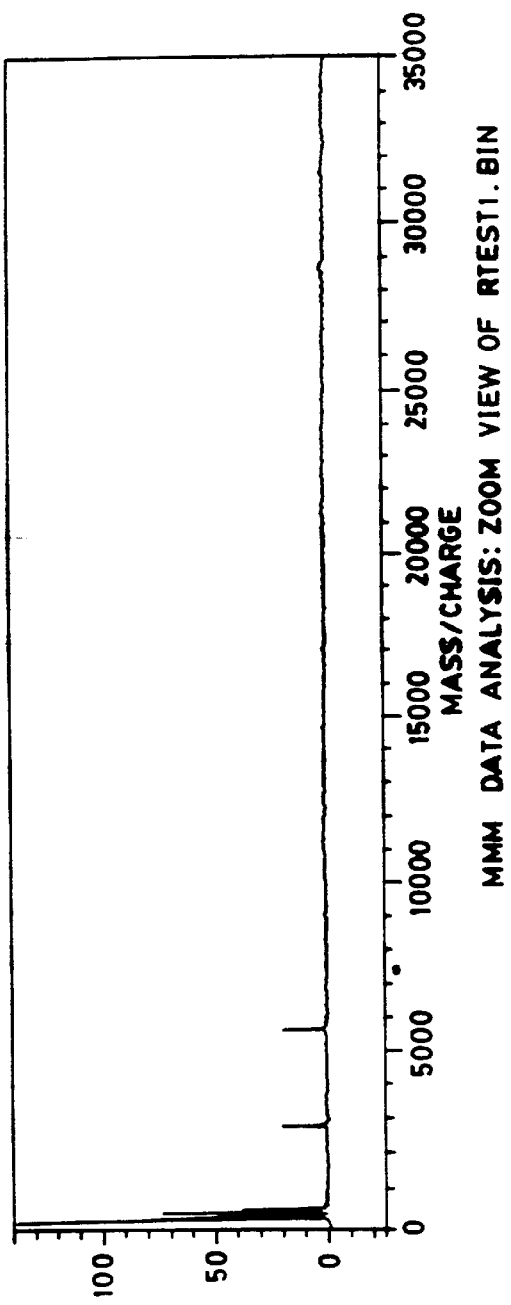
FIG. 6a and 6b are mass spectrum obtained with insulin on a thin precast film of cellulose nitrate and matrix on a glass disc substrate.
Figure 6B:
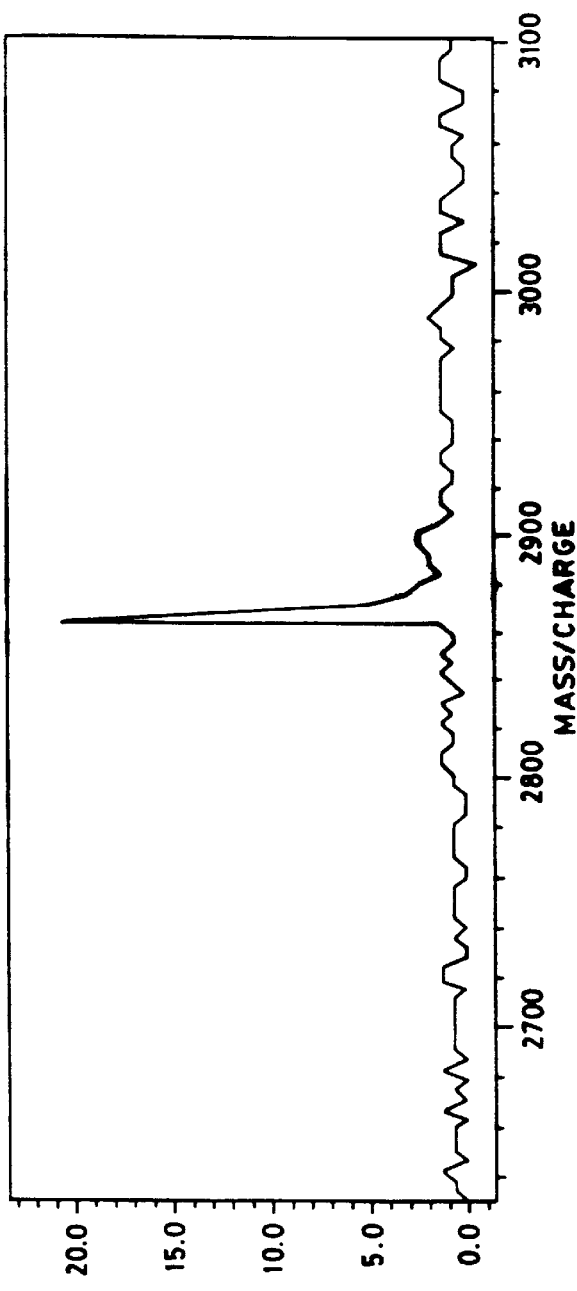

Construction of Thin Films of α-cyano-4-hydroxycinnamic acid and Cellulose Nitrate These thin films were prepared according to the procedure of Example 1 except that the solution of cellulose nitrate and α-cyano-4-hydroxycinnamic acid was prepared in a mixture of 75% anhydrous ether and 25% ethanol by volume. A spectrum from insulin deposited on such a thin film is shown in FIGS. 6a and 6b. FIG. 6b is a magnified or zoom view of the spectra of FIG. 6a at approximately 2700 to 30000 mass/charge.

Example 3

Construction of Thin Films using Polycarbonate and α-cyano-4-hydroxycinnamic acid These thin films are prepared according to the procedure of Example 1 except that the solution of polycarbonate α-cyano-4-hydroxycinnamic acid was prepared in tetrahydrofuran. Although the invention has been described by way of illustration and example for purposes of clarity and understanding, it will be obvious that certain changes and modifications may be practiced within the scope of the invention, as limited only by the scope of the following appended claims.

We claim:

1. A thin film for receiving a sample for analysis by matrix-assisted laser desorption mass spectrometry comprising crystals of a matrix material dispersed in a support material, said thin film having a thickness of 0.005 to 5 μm and said crystals selected from at least one of the group consisting of sinapinic acid and α-cyano-4-hydroxycinnamic acid, said film promoting resolution and/or reproducibility of mass spectrometry analysis.

2. The thin film of claim 1 wherein said support material limits the growth of matrix crystals.

3. The thin film of claim 2 wherein said support material comprises a polymer.

4. The thin film of claim 1 wherein said support material comprises a microreticulated surface.

5. A thin film for receiving a sample for analysis by matrix-assisted laser desorption mass spectrometry, comprising a matrix material polymer composition disposed upon a substrate wherein the matrix material is selected from at least one of the group consisting of sinapinic acid and α-cyano-4-hydrocinnamic acid, and is dispersed within said polymer as crystals, said thin film having a thickness from 0.005 to 5 μm, said thin film promoting resolution and/or reproducibility of mass spectrometry analysis.

6. The thin film of claim 5 wherein said matrix-polymer composition has a thickness of not greater than 1 μm.

7. The thin film of claim 5 wherein said matrix polymer composition comprises a polymer selected from the group consisting of cellulose acetate, cellulose nitrate, and polycarbonate.

8. The thin film of claim 5 wherein said matrix-polymer composition ranges from about 70% polymer to about 30% polymer.

9. A device for performing matrix-assisted laser desorption mass spectrometry of sample molecules, comprising a substrate capable of receiving on its surface said thin film of claim 5.

10. The device of claim 9 further comprising said thin film and sample molecules, wherein the sample molecules and the matrix material polymer composition are substantially coplanar.

11. The device of claim 9 wherein said substrate is selected from the group consisting of glass, ceramic, plastic and metal.

12. The device of claim 9 wherein said thin film is relatively thin and uniform, whereby the device is resistant to decreased mass resolution and sensitivity.

13. A thin film for receiving sample for analysis by matrix-assisted laser desorption mass spectrometry, said thin film comprising a matrix material dispersion disposed on substrate, where said thin film is formed by depositing a solution containing matrix material, a support material and solvent upon a spinning substrate at a deposition rate sufficient to allow evaporation of said solvent, thereby forming a thin film of said dispersion of said matrix within said support material, said film having a thickness of 0.005 to 5 μm and said matrix material comprising crystals selected from the group consisting of sinapinic acid and α-cyano-4-hydrocinnamic acid.

14. The thin film of claim 13 wherein said film has a thickness of not greater then 1 μm.

15. The thin film of claim 13 wherein said support material limits the size of crystals of matrix material.

16. The thin film of claim 13 wherein said support material comprises a microreticulated surface.

17. The thin film of claim 13 wherein said matrix material-support material dispersion comprises a polymer selected from the group consisting of cellulose acetate, cellulose nitrate, and polycarbonate.

18. The thin layer of claim 13, wherein said matrix is selected from the group consisting of sinapinic acid and α-cyano-4-hydrocinnamic acid.

* * * * *